United States Patent
Harada

(10) Patent No.: US 6,712,766 B2
(45) Date of Patent: Mar. 30, 2004

(54) ULTRASONIC PROBE

(75) Inventor: Yasukazu Harada, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/410,205

(22) Filed: Apr. 10, 2003

(65) Prior Publication Data

US 2003/0195419 A1 Oct. 16, 2003

(30) Foreign Application Priority Data

Apr. 11, 2002 (JP) ........................................ 2002-109217

(51) Int. Cl.$^7$ ................................................. A61B 8/14
(52) U.S. Cl. ........................ 600/459; 604/22; 600/462
(58) Field of Search ................................. 600/437, 462, 600/463, 439, 568, 471, 467, 459

(56) References Cited

U.S. PATENT DOCUMENTS

| | | | |
|---|---|---|---|
| 4,794,931 A | | 1/1989 | Yock |
| 5,000,185 A | | 3/1991 | Yock |
| 5,115,814 A | * | 5/1992 | Griffith et al. ............... 600/463 |
| 5,313,949 A | | 5/1994 | Yock |
| 5,372,138 A | * | 12/1994 | Crowley et al. ............. 600/463 |
| 5,582,178 A | | 12/1996 | Yock |
| 5,588,432 A | * | 12/1996 | Crowley ..................... 600/439 |
| 5,651,364 A | | 7/1997 | Yock |
| 5,676,151 A | | 10/1997 | Yock |
| 5,715,825 A | * | 2/1998 | Crowley ..................... 600/462 |
| 5,865,178 A | | 2/1999 | Yock |
| 5,902,245 A | | 5/1999 | Yock |
| 6,007,514 A | * | 12/1999 | Nita .............................. 604/22 |
| 6,086,544 A | * | 7/2000 | Hibner et al. ................ 600/568 |
| 6,221,015 B1 | | 4/2001 | Yock |
| 6,409,673 B2 | | 6/2002 | Yock |
| 6,572,554 B2 | | 6/2003 | Yock |

* cited by examiner

*Primary Examiner*—Dennis W. Ruhl
*Assistant Examiner*—Ruby Jain
(74) *Attorney, Agent, or Firm*—Burns, Doane, Swecker & Mathis, L.L.P.

(57) ABSTRACT

An ultrasonic probe includes a sheath having a distal end insertable in a body cavity or a lumen, a proximal end having an injection port allowing an ultrasonic wave propagating liquid to be injected through the injection port, and a passage extending from the proximal end to the distal end, a drive shaft, having a distal end and a proximal end, for transmitting a mechanical drive force from the proximal end to the distal end, the drive shaft being disposed in the passage of the sheath, and an ultrasonic transducer provided at the distal end of the drive shaft, wherein a gap between the inner surface of the passage and the outer periphery of the drive shaft on the distal end side of the sheath is smaller than that on the proximal end side of the sheath. Such an ultrasonic probe is advantageous in efficiently discharging bubbles remaining in the sheath with less water flow, and also reducing the diameter of the ultrasonic probe while keeping a high quality of an ultrasonic tomogram.

6 Claims, 3 Drawing Sheets

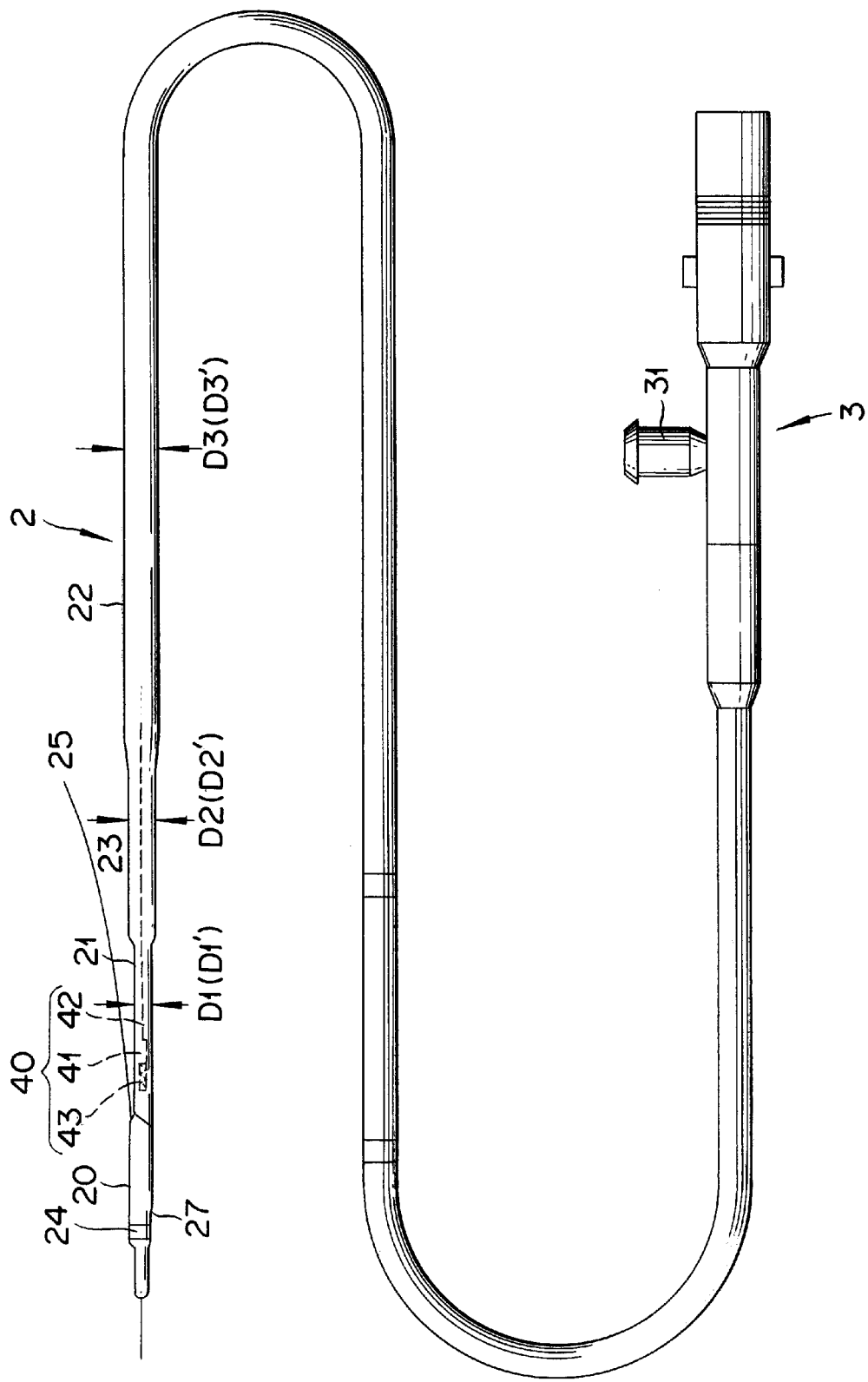

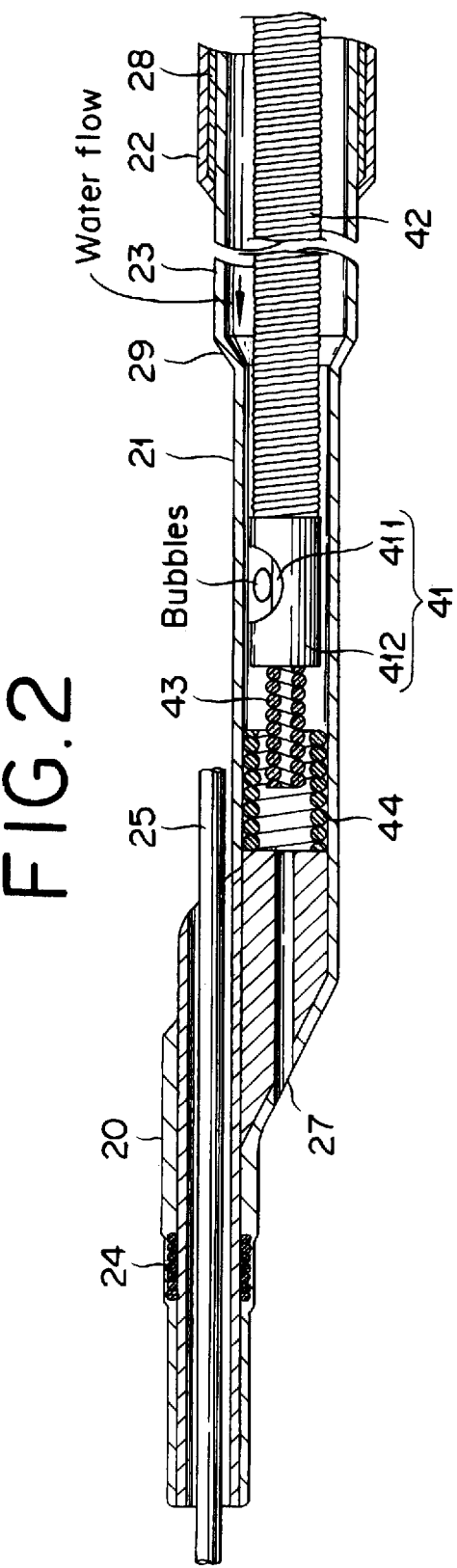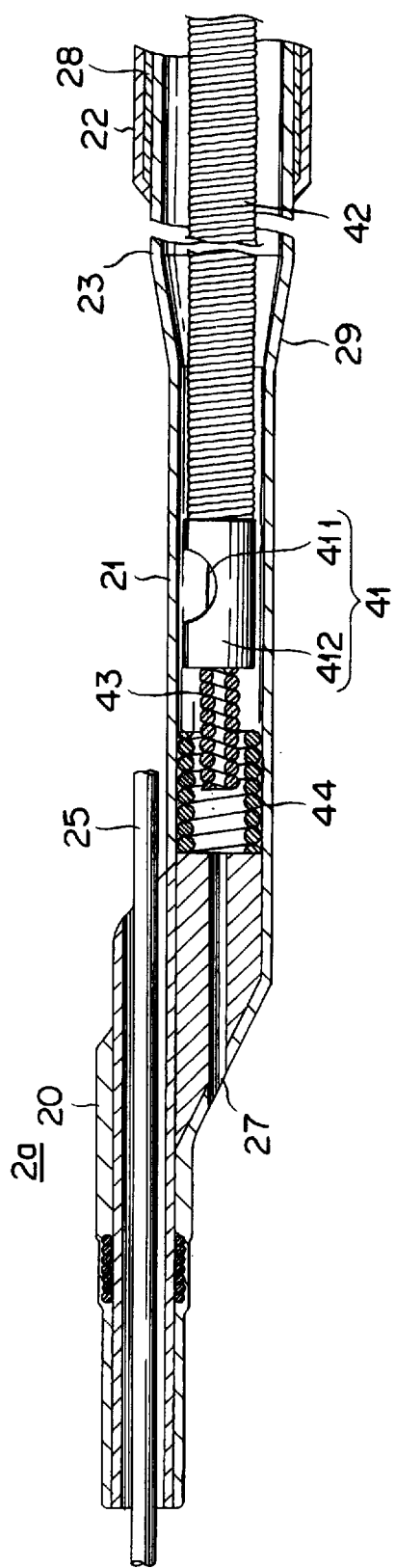

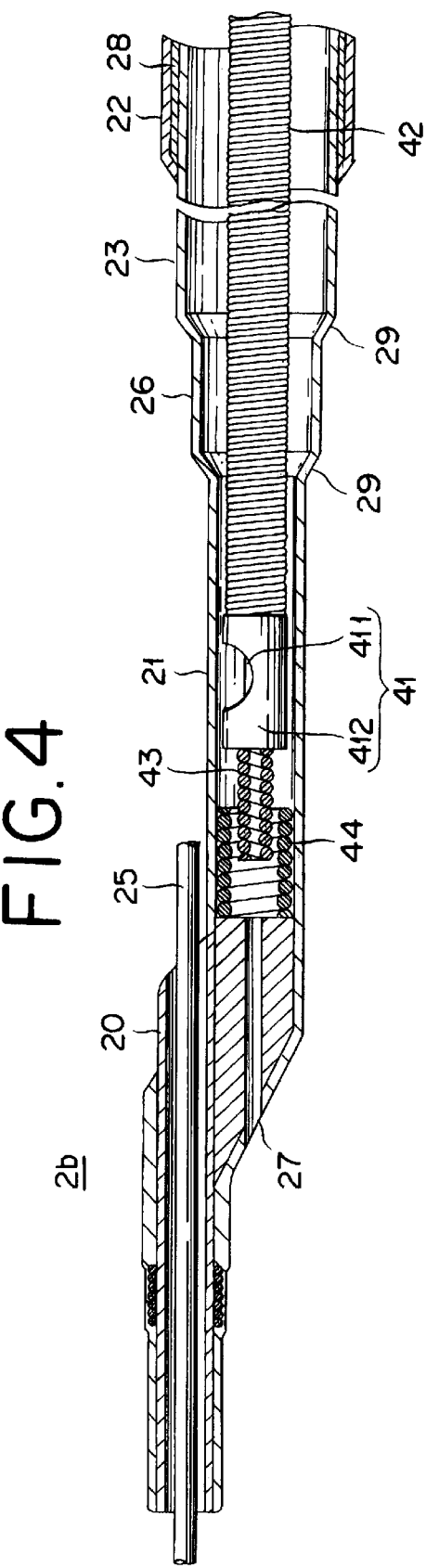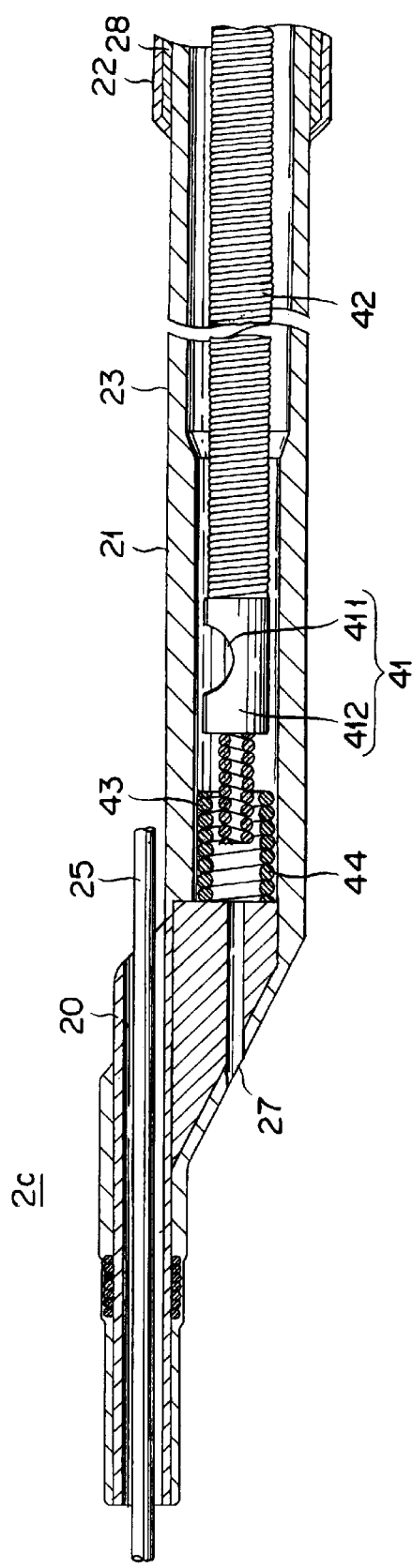

ULTRASONIC PROBE

BACKGROUND OF THE INVENTION

1. Field of the Invention

The present invention relates to an ultrasonic imaging probe used to be inserted in a body cavity or a lumen, such as a blood vessel, a vas, or a digestive organ, and to display a tomogram of the body cavity or the lumen.

2. Description of the Related Art

To treat angiostenosis portions taken as causes of cardiac infarction and the like, there have been used methods of performing percutaneous procedure for affected portions by using catheters, for example, a method of expanding an angiostenosis portion with a dilatation catheter having a balloon at its distal end, a method of implanting a tiny mesh tube called "stent" in an angiostenosis portion, or a method of resecting an angiostenosis portion by rotating a grinder or a cutter using an instrument called "atherectomy device". Of these methods, a suitable one has been selected in accordance with the state of an angiostenosis portion and the state of a patient.

The ultrasonic probe has been mainly used in such percutaneous treatment of an angiostenosis portion for the purpose of observing the state of the angiostenosis portion so as to assist the decision to select the most suitable treatment means, and also observing the state of the angiostenosis portion after treatment.

The ultrasonic probe includes a flexible imaging core (having an ultrasonic transducer unit for transmitting and receiving ultrasonic waves to and from an affected portion and a drive shaft for rotating the ultrasonic transducer unit), and a sheath for covering the imaging core.

The inspection using an ultrasonic probe generally involves previously advancing a guide wire to an angiostenosis portion as an affected portion, carrying an ultrasonic transducer unit positioned in the vicinity of the distal end of the ultrasonic probe along the guide wire, and operating the ultrasonic transducer unit, thereby obtaining a continuous ultrasonic tomogram across the affected portion.

The ultrasonic probe fails to acquire an image signal unless an ultrasonic wave propagating substance for propagating ultrasonic waves is present between the ultrasonic transducer and the wall of a blood vessel, and therefore, a priming work of replacing air in the sheath with a liquid such as physiological saline is performed before insertion of the ultrasonic probe in a patient.

If the priming work is insufficient and thereby micro-sized bubbles remain on the surface of the ultrasonic transducer, the bubbles strongly reflect ultrasonic waves, to shield or scatter the ultrasonic waves, thereby significantly disturbing an image. For this reason, it is required to discharge bubbles from the sheath as much as possible.

To cope with such a problem, there has been proposed a method of enlarging a gap between the flexible imaging core and the inner wall surface of a sheath as much as possible, to ensure a specific flow rate of a liquid at the time of injecting the liquid from the proximal end side of the sheath, thereby removing bubbles remaining on the ultrasonic transducer unit by water flow.

This method, however, has a problem that if the gap between the flexible imaging core and the inner wall surface of the sheath is enlarged, the outer diameter of the sheath becomes necessarily large, to degrade the ability of the sheath to pass through a small-diameter blood vessel affection portion or to reach such a small-diameter blood vessel affection portion. In this way, there exist two inconsistent requirements of enlarging the flow passage for priming and reducing the outer diameter of the probe.

Another problem of the conventional sheath is that since the sheath, if used for a blood vessel, is as long as a value in a range of about 120 mm to 180 mm, even when a priming liquid is injected at a high pressure on the proximal end side, the pressure cannot be transmitted to the vicinity of an ultrasonic transducer on the distal end side, thereby failing to perfectly remove bubbles remaining on the ultrasonic transducer.

SUMMARY OF THE INVENTION

An object of the present invention is to provide an ultrasonic probe capable of efficiently discharging bubbles remaining inside the probe with less water flow, and also capable of reducing the diameter of the probe while keeping a high quality of an ultrasonic tomogram.

To achieve the above object, according to an aspect of the present invention, there is provided an ultrasonic probe including a sheath having a distal end insertable in a body cavity or a lumen, a proximal end having an injection port allowing an ultrasonic wave propagating liquid to be injected through the injection port, and a passage extending from the proximal end to the distal end, a drive shaft, having a distal end and a proximal end, for transmitting a mechanical drive force from the proximal end to the distal end, the drive shaft being disposed in the passage of the sheath, and an ultrasonic transducer provided at the distal end of the drive shaft, wherein a gap between the inner surface of the passage and the outer periphery of the drive shaft on the distal end side of the sheath is smaller than that on the proximal end side of the sheath.

With this configuration, since the flow passage is formed such that the gap between the outer periphery of the drive shaft provided in the sheath and the inner surface of the sheath becomes narrower on the distal end side than on the proximal end side, the flow characteristics such as the flow velocity, flow rate, and the flow pressure of the ultrasonic wave propagating liquid flowing from the proximal end are rapidly improved at a portion where the gap becomes narrow, and the flow characteristics of the ultrasonic wave propagating liquid are also improved in the vicinity of the transducer unit. Accordingly, it is possible to remove bubbles remaining in the vicinity of the ultrasonic transducer by the flow of the ultrasonic wave propagating liquid, and hence to keep a high quality of an ultrasonic tomogram formed by the ultrasonic transducer.

The passage preferably has a change portion whose inner diameter is changed.

With this configuration, since the flow passage becomes narrower on the distal end side than on the proximal end side, the center axis of the sheath is more closely aligned with the drive axis of the drive shaft, with a result that the drive of the drive shaft provided in the sheath can be stabilized at the distal end. As a result, it is possible to form a stable ultrasonic tomogram by the ultrasonic transducer.

The outer diameter of the sheath at the distal end is preferably smaller than that at the proximal end.

With this configuration, since the outer diameter of the sheath is smaller on the distal end side than on the proximal end side, it is possible to easily insert the sheath in a body cavity or a lumen.

The ultrasonic probe preferably further includes a discharge port allowing air in the sheath and/or the ultrasonic wave propagating liquid to be discharged out of the discharge port.

With this configuration, since the discharge port for allowing air in the sheath and/or the ultrasonic wave propagating liquid to be discharged out of the discharge port is provided at the distal end of the sheath, it is possible to remove air remaining in the sheath, together with the ultrasonic wave propagating liquid, by the flow of the ultrasonic wave propagating liquid.

BRIEF DESCRIPTION OF THE DRAWINGS

The above and other objects, features, and advantages of the present invention become more apparent from the following detailed description in conjugation with the accompanying drawings, wherein:

FIG. 1 is a view showing an ultrasonic probe of the present invention;

FIG. 2 is an enlarged view a portion of a distal end of the ultrasonic probe;

FIG. 3 is an enlarged view of a portion of the distal end of the ultrasonic probe for illustrating a modification of a sheath;

FIG. 4 is an enlarged view of a portion of the distal end of the ultrasonic probe for illustrating another modification of a sheath; and FIG. 5 is an enlarged view of a portion of the distal end of the ultrasonic probe for illustrating a further modification of a sheath.

DETAILED DESCRIPTION OF THE PREFERRED EMBODIMENTS

Hereinafter, preferred embodiments of the present invention will be described with reference to the drawings.

FIG. 1 is a view showing an ultrasonic probe of the present invention. FIG. 2 is an enlarged view showing a portion of a distal end of an ultrasonic probe. It is to be noted that in FIG. 2, the portion of the distal end of the ultrasonic probe is depicted on a scale partially different from that shown in FIG. 1 for clarity of the feature of the present invention.

An ultrasonic probe 1 includes a sheath 2 to be inserted in a body cavity, and a hub 3 not inserted in a body cavity but located on the user's side in order to be operated by a user.

The sheath 2 has a sheath distal end 21, a sheath main body 22, and a sheath intermediate portion 23. The sheath intermediate portion 23 is connected between the sheath distal end 21 and the sheath main body 22. The sheath main body 22 is connected to the hub 3. A guide wire lumen 20 is provided at the tip of the sheath distal end 21.

The guide wire lumen 20 has a hole (lumen) in which a guide wire 25 is insertable. The guide wire 25 is previously inserted in a body cavity for introducing the ultrasonic probe 1 to an affected portion. To be more specific, the ultrasonic probe 1 is introduced to an affected portion by means of the guide wire 25 passing through the guide wire lumen 20. A radiopaque marker 24 is buried in a wall of the guide wire lumen 20 in order to allow a user to observe, when the ultrasonic probe 1 is inserted in a body cavity, the position of the distal end of the ultrasonic probe under X-ray fluoroscopic guidance.

A discharge port 27 is formed at the tip of the sheath distal end 21, which tip is equivalent to a boundary with the guide wire lumen 20. An ultrasonic wave propagating liquid supplied to fill the sheath 2 over the length from the proximal end to the distal end is discharged out of the discharge port 27. An ultrasonic transducer 411 for acquiring an image is provided in a passage of the sheath distal end 21. The sheath main body 22 is formed by covering the extended portion of the sheath intermediate portion 23 with a reinforcing layer 28 made from a metal pipe or a metal wire braid. The sheath main body 22 is connected to the hub 3. The outer diameter (D1) of the sheath distal end 21, the outer diameter (D2) of the sheath intermediate portion 23, and the outer diameter (D3) of the sheath main body 22 have a relationship of D1 <D2<D3. For example, the outer diameters D1, D2, and D3 are set to 0.8 mm, 0.87 mm, and 1.04 to 1.06 mm, respectively.

The sheath distal end 21 is connected to the sheath intermediate portion 23 at a boundary 29. The wall thickness of the sheath 2 is kept constant in a region of the sheath distal end 21 to the sheath intermediate portion 23, and therefore, the inner diameter (D1') of the sheath distal end 21 and the inner diameter (D2') of the sheath intermediate portion 23 have a relationship of D1'<D2', which corresponds to the outer diameter relationship of D1<D2. The inner diameter (D3') of the sheath main body 22 is equal to the inner diameter (D2') of the sheath intermediate portion 23.

An imaging core 40 is housed in the sheath 2. The imaging core 40 includes a transducer unit 41, a drive shaft 42, and a rotation stabilizing coil 43. The transducer unit 41 has the ultrasonic transducer 411 for transmitting and receiving ultrasonic waves to and from a tissue in a body cavity. The drive shaft 42 is adapted to rotate the transducer unit 41 mounted to the distal end of the drive shaft 42. The rotation stabilizing coil 43 is mounted to the distal end side of the transducer unit 41.

The transducer unit 41 is, as shown in FIG. 2, composed of the ultrasonic transducer 411 for transmitting/receiving ultrasonic waves, and an ultrasonic transducer housing 412 for housing the ultrasonic transducer 411.

The ultrasonic transducer 411 is adapted to generate ultrasonic waves propagating toward the interior of the body and receive the ultrasonic waves reflected and returned therefrom, and hence to form an ultrasonic tomogram of an affected portion. The ultrasonic transducer housing 412 is formed into a recessed shape, and the ultrasonic transducer 411 is held in and protected by the recessed portion of the ultrasonic transducer housing 412.

The drive shaft 42 is characterized by being flexible and capable of transmitting a rotational power generated by a motor (unshown) connected with the hub 3 to the transducer unit 41, and is formed of a multi-layer coil shaped tube having a constant outer diameter. In this embodiment, the multi-layer coil-shaped tube is exemplified by three-layer coils wound with the winding directions alternately changed. For example, the three-layer coils are composed of a combination of a right hand coil, a left hand coil, and a right hand coil. The drive shaft 42 transmits a rotational power from the hub 3 to the transducer unit 41, to rotate the transducer unit 41, thereby allowing a user to observe an affected portion in a body cavity such as a blood vessel or a vas at 360 degrees. A signal line for transmitting a signal detected by the transducer unit 41 to the hub 3 passes through the drive shaft 42.

The rotation stabilizing coil 43 is mounted to the distal end of the transducer unit 41. When the imaging coil 40 is rotated, the coil 43 functions as a guide for allowing the transducer unit 41 to be stably rotated.

A radiopaque marker 44 is mounted to a portion, on the distal end side of the transducer unit 41, of the inner wall of the sheath 2. When the ultrasonic probe 1 is inserted in a body cavity, the position of the transducer unit 41 can be observed by means of the radiopaque marker 44 under X-ray fluoroscopic guidance.

The hub 3 has a port 31 for supplying an ultrasonic wave propagating liquid in the sheath 2 therethrough. The ultrasonic wave propagating liquid supplied from the port 31 flows to the sheath distal end 21 through the sheath main body 22, that is, flows from the proximal end side to the distal end side of the sheath 2, to fill the inside of the sheath 2 throughout from the proximal end side to the distal end side. Since the sheath 2 is first filled with an ultrasonic wave propagating liquid and is then inserted in a body cavity or the like, the ultrasonic wave propagating liquid is present between the ultrasonic transducer 411 and the wall of a blood vessel, to allow ultrasonic waves to be transmitted to an affected portion via the ultrasonic wave propagating liquid and to be reflected and returned therefrom. In other words, the transducer unit 41 can acquire an image signal due to ultrasonic waves by the presence of the ultrasonic wave propagating liquid.

The ultrasonic wave propagating liquid is represented by physiological saline which does not exert adverse effect on a human body even if it is discharged in the body from the discharge port 27.

The hub 3 holds the drive shaft 42, and transmits a rotational power of the motor connected with the hub 3 to the transducer unit 41 via the drive shaft 42.

The sheath 2 having the feature of the present invention will be more fully described with reference to FIG. 2.

As shown in FIG. 2, the sheath 2 is formed such that the sheath distal end 21 is thinner than the sheath intermediate portion 23. Here, the wall thickness of the sheath 2 is kept approximately constant, and the outer diameter of the drive shaft 42 is kept approximately constant. As a result, a passage for allowing the flow of an ultrasonic wave propagating liquid therethrough, which passage is formed between the inner surface of the sheath 2 and the surface of the drive shaft 42 is narrower on the sheath distal end 21 side than on the sheath intermediate portion 23 side. The boundary 29, which connects the sheath distal end 21 to the sheath intermediate portion 23, has a smooth taper shape.

To reduce the diameter of the sheath 2 stepwise in the direction from the sheath intermediate portion 23 to the sheath distal end 21 by providing a stepped portion therebetween, the sheath 2 is subjected to a stepped portion forming work at the time of producing the sheath 2. To be more specific, a straight-line shaped core is inserted in a straight-line shaped tube and the tube is inserted in a die having a hole whose diameter is narrower than the diameter of the tube. At this time, both the inner diameter and the outer diameter of the sheath 2 can be reduced by heating the die. The sheath 2 can be tapered by changing the winding speed.

Conventionally, since any stepped portion forming work has not been performed at the time of producing the sheath, the inner diameter side of the sheath has been straightened without any stepped portion. On the contrary, according to the present invention, the diameter of the flow passage formed in the sheath is stepwise reduced in the direction from the sheath intermediate portion 23 to the sheath distal end 21.

The flow passage of the sheath 2 is stepwise narrowed as described above. More specifically, a gap between the inner surface of the sheath 2 and the outer periphery of the imaging core 40 (which is formed in the sheath 2 and has the constant outer diameter) becomes smaller on the sheath distal end 21 side than on the sheath intermediate portion 23 side. This is advantageous as follows: namely, on the proximal end side from the sheath intermediate portion 23 side, since the gap is larger, the cross-sectional area of the flow passage of the ultrasonic wave propagating liquid is larger, with a result that the ultrasonic wave propagating liquid can be easily injected; and at the boundary 29 where the gap become small, the flow characteristics such as the flow velocity, the flow rate, and the flow pressure of the ultrasonic wave propagating liquid flowing from the sheath intermediate portion 23 side are rapidly improved and thereby in the vicinity of the transducer unit 4, the flow characteristics of the ultrasonic wave propagating liquid are also improved.

Since the transducer unit 41 is formed into a recessed shape, even if the sheath 2 is filled with the ultrasonic wave propagating liquid, bubbles are liable to remain in the recessed portion. If such bubbles remain in the recessed portion, ultrasonic waves oscillated from the transducer unit 41 cannot pass through the bubbles, resulting in degradation of an ultrasonic tomogram of an affected portion.

According to the present invention, however, since the flow characteristics in the vicinity of the ultrasonic transducer 41 can be improved, it is possible to easily, efficiently remove bubbles with less water flow passing through the narrow passage, and hence to keep a high quality of an ultrasonic tomogram formed by the imaging core 40.

The flow passage formed in the sheath 2 is specified such that the gap between the outer periphery of the imaging core 40 and the inner surface of the sheath 2 becomes small at the sheath distal end 21, so that the center axis of the sheath distal end 21 is more closely aligned with the rotational axis of the drive shaft 42. Accordingly, when a rotational power is transmitted to the drive shaft 42, the drive shaft 42 can be stably rotated without occurrence of eccentric motion. As a result, a stable ultrasonic tomogram can be obtained by the imaging core 40.

With respect to the sheath 2, not only the inner diameter (that is, the diameter of the flow passage formed in the sheath 2) but also the outer diameter becomes smaller on the sheath distal end 21 side than on the sheath intermediate portion 23 side. As a result, the sheath 2 can be easily inserted in a body cavity or a lumen.

The length of the sheath distal end 21 in the axial direction is preferable to be in a range of 0.2 to 2.4 inches. If the length is shorter than 0.2 inch, a portion in which the ultrasonic transducer 411 is housed fails to be sufficiently introduced in a fine-diameter portion of a blood vessel to be diagnosed, whereas if the length is longer than 2.4 inches, it is difficult to flow the ultrasonic wave propagating liquid over the sheath distal end 21. The total length of the sheath distal end 21 and the sheath intermediate portion 23 in the axial direction is preferable to be in a range of 0.2 to 8 inches. If the total length is shorter than 0.2 inch, it is difficult to insert the sheath 2 to an angiostenos is portion of the coronary of a heart to be diagnosed, whereas if the total length is longer than 8 inches, there may occur a kink of the sheath 2 during insertion of the sheath 2.

To achieve the effect of the present invention, the inner diameter of the sheath distal end 21 is preferable to be 55 to 99% of the inner diameter of the sheath intermediate portion 23.

Bubbles in the sheath 2 can be discharged together with the ultrasonic wave propagating liquid from the discharge port 27 (specialized for discharging air and/or an ultrasonic wave propagating liquid) provided in the sheath distal end 21.

Various modifications of the above-described embodiment of the present invention will be described below.

FIGS. 3 to 5 are enlarged views each showing a portion of the distal end of the ultrasonic probe for illustrating the modifications of the sheath 2.

A sheath 2a shown in FIG. 3 is different from the sheath 2 shown in FIG. 2 in that a stepped portion formed between the sheath distal end 21 and the sheath intermediate portion 23 is configured as a smooth long taper portion. Since the stepped portion has the smooth long taper, the flow characteristics of the ultrasonic wave propagating liquid on the sheath distal end 21 side are improved, with a result that like the sheath 2 shown in FIG. 2, bubbles on the transducer unit 41 can be removed. In addition, since the region in which the outer diameter is small becomes longer, the sheath 2a is easy to be inserted in a body cavity or a lumen.

In a sheath 2b shown in FIG. 4, a sheath connection portion 26 is further formed between the sheath distal end 21 and the sheath intermediate portion 23. Each of the inner diameter (which is the diameter of the flow passage) and the outer diameter of the sheath 2 becomes stepwise smaller in the order of the sheath intermediate portion 23, the sheath connection portion 26, and the sheath distal end 21.

The flow characteristics are improved when the ultrasonic wave propagating liquid flows from the sheath intermediate portion 23 to the sheath connection portion 26 and when it flows from the sheath connection portion 26 to the sheath distal end 21 respectively, so that it is possible to remove bubbles on the transducer unit 41 like the sheath 2 shown in FIG. 2. In addition, since the region in which the outer diameter is small becomes longer, the sheath 2b can be easily inserted in a body cavity or a lumen.

In FIG. 4, the diameter of the sheath 2b is reduced in three-steps; however, the present invention is not limited but may be configured such that the diameter of the sheath 2 may be reduced in a plurality (four or more) of steps.

A sheath 2c shown in FIG. 5 is different from the sheath 2 shown in FIG. 2 in that any stepped portion is not provided between the outer diameter of the sheath distal end 21 and the outer diameter of the sheath intermediate portion 23. In this sheath 2c, however, a stepped portion is provided between the inner diameter of the sheath distal end 21 and the inner diameter of the sheath intermediate portion 23 (that is, on the diameter of the flow passage of the ultrasonic wave propagating liquid) by changing the wall thickness of the sheath 2c there between.

With such a stepped portion, the flow passage for the ultrasonic wave propagating liquid become narrow in the direction from the sheath intermediate portion 23 to the sheath distal end 21, so that the flow characteristics are improved at a portion where the flow passage becomes narrow, thereby removing bubbles remaining on the transducer unit 41 like the sheath 2 shown in FIG. 2.

As described above, according to the present invention, since the flow passage for allowing the flow of an ultrasonic wave propagating liquid therethrough is narrowed in the vicinity of the transducer unit 41 of the imaging core 40, it is possible to improve the flow characteristics of the ultrasonic wave propagating liquid and hence to discharge bubbles remaining on the transducer unit 41. This is advantageous in keeping a high quality of an ultrasonic tomogram formed by the imaging core 40.

Although the present invention has been described by example of the ultrasonic probe including the imaging core 40 not movable forward and backward in the axial direction in the sheath 2, the present invention is not limited thereto but may be applied to an ultrasonic probe including an imaging core movable forward and backward in the axial direction in the sheath 2.

In this case, there may be provided as stepped portion capable of narrowing the flow passage in the vicinity of the proximal end side of the transducer unit 41 in a state that the imaging core is most inserted in the sheath or most pulled from the sheath. With such a stepped portion, it is possible to improve the flow characteristics of an ultrasonic wave propagating liquid passing through the transducer unit 41, and hence to discharge bubbles remaining on the transducer unit 41. It is to be noted that the position of the stepped portion may be freely changed.

While the preferred embodiments have been described using specific terms, such description is for illustrative purposes only, and it is to be understood that changes and variations may be made without departing from the spirit or scope of the following claims.

This application is based on Japanese Patent Application No. 2002-109217 filed on Apr. 11, 2002, the contents of which are hereby incorporated by reference.

What is claimed is:

1. An ultrasonic probe comprising:

a sheath having a distal end insertable in a body cavity or a lumen, a proximal end, and a passage extending from said proximal end to said distal end;

a hub connected to the proximal end of said sheath and furnished with an injection port for injecting an ultrasonic wave propagating liquid;

a drive shaft, having a distal end and a proximal end, for transmitting a mechanical drive force from said proximal end to said distal end, said drive shaft being disposed in said passage of said sheath; and an ultrasonic transducer provided at said distal end of said drive shaft;

wherein a gap between an inner surface of said passage and an outer periphery of said drive shaft on said distal end side of said sheath is smaller than that on said proximal end side of said sheath.

2. An ultrasonic probe according to claim 1, wherein said passage of said sheath has a change portion whose inner diameter is changed.

3. An ultrasonic probe according to claim 2, wherein the outer diameter of said sheath at said distal end is smaller than that at said proximal end.

4. An ultrasonic probe according to claim 1, further comprising a discharge port allowing air in said sheath and/or said ultrasonic wave propagating liquid to be discharged out of said discharge port.

5. An ultrasonic probe according to claim 2, further comprising a discharge port allowing air in said sheath and/or said ultrasonic wave propagating liquid to be discharged out of said discharge port.

6. An ultrasonic probe according to claim 3, further comprising a discharge port allowing air in said sheath and/or said ultrasonic wave propagating liquid to be discharged out of said discharge port.

* * * * *